Figure 2:
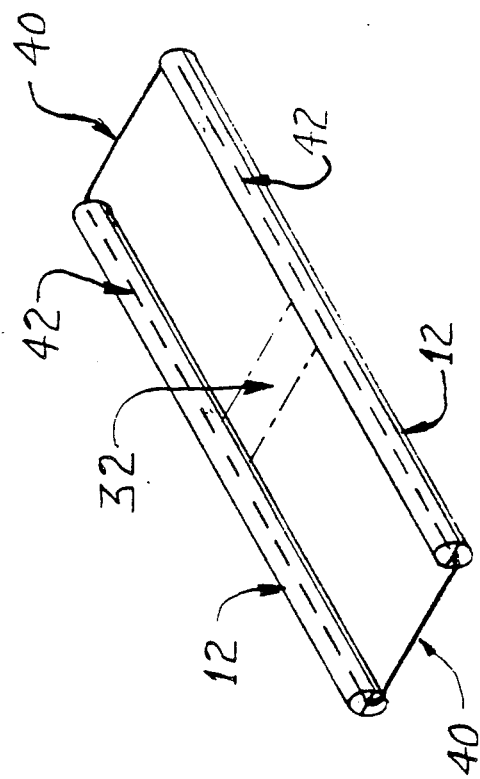

United States Patent [19]

Wyss

[11] Patent Number: 5,123,432
[45] Date of Patent: Jun. 23, 1992

[54] DISPOSABLE FLOSSING TOOL FEATURING LEVERAGE ACTION

[76] Inventor: John R. Wyss, 4020-148th Ave. NE., Suite F, Redmond, Wash. 98052

[21] Appl. No.: 568,711

[22] Filed: Aug. 16, 1990

Related U.S. Application Data

[63] Continuation-in-part of Ser. No. 421,352, Oct. 13, 1989, abandoned.

[51] Int. Cl.⁵ .............................................. A61C 15/00
[52] U.S. Cl. .................................................... 132/323
[58] Field of Search ................. 132/323, 326, 327, 324

[56] References Cited

U.S. PATENT DOCUMENTS

| | | | |
|---|---|---|---|
| 2,180,522 | 11/1939 | Henne | 132/323 |
| 3,892,249 | 7/1975 | Jones et al. | 132/323 |
| 4,006,750 | 2/1977 | Chodorow | 132/323 |
| 4,192,330 | 3/1980 | Johnson | 132/323 |
| 4,982,752 | 1/1991 | Rodriguez | 132/324 |

*Primary Examiner*—Cary E. O'Connor

[57] ABSTRACT

A double-ended hand held flossing tool with stressing means is provided which uses a loop of floss made integral with the frame members of the tool, and provides stressing action through fingertip manipulation of the members. The loop is integral and structural to the tool, thus my tool design gains the advantage of stability by virtue of two members being integral with a floss loop molded directly into the construction of the frame members of the tool.

2 Claims, 1 Drawing Sheet

DISPOSABLE FLOSSING TOOL FEATURING LEVERAGE ACTION

This application is a continuation in part of the application of the same title filed Oct. 13, 1989, Ser. No. 07/421,352 abandoned.

BACKGROUND OF THE INVENTION

The present invention is in the field of dental floss holders and more particularly those having leverage means of stressing the floss with tension for the purpose of increasing the utility of the floss and improving user control of the floss while the floss is used to clean spaces between the teeth and periodontal regions, aiding greatly in the reduction of tooth decay, gum diseases and gingivitis.

Prior art teaches methods of manufacturing flossing tools which make use of fulcrum means between the portion which is held by the user, being a "U"-shaped handle, and the portion which holds the floss, being a bifurcated extension. One such design is taught by Johnson, U.S. Pat. No. 4,192,330, filed Mar. 11, 1980. In the same filing, a way to use a loop of floss as a removable insert is described, for the purpose of refilling the floss holder with fresh floss when the floss is frayed or used up. The floss loops around the floss holder portion of the tool and is held in place by "grooves of arms 122 and 124 and under terminal retention lips 138 at the junction 140". When the handle of the holder is collapsed the bifurcated extension spreads, and a tension is placed upon the floss, causing the floss to be stretched taut. Said tensioning of the floss is beneficial in the use of flossing tools, as taught in a number of patents in addition to Johnson. Among the others: N. S. Brody, U.S. Pat. Nos. 2,811,162, filed Oct. 29, 1957; Yafai, 4,304,246, filed Dec. 8, 1981; Schiff, D251,074, filed Feb. 13, 1979; Badoux, 4,736,757, Apr. 12, 1988.

In the Yafai patent, a loop of floss is used, as in the Johnson patent, and held in its place by a spur 30 and trough-like configuration at the base of the frame 11a of the Dental Floss Holder.

A number of the other devices use a short strand of floss which is not a loop, but held at each end by affixing the ends of the strand to prongs, as in Badoux, or by molding the plastic of the holder about the ends of the strand of floss, as illustrated in the design patent by Schiff. However, the slippery nature of dental floss, made up of many finer strands, often permits it to slide from its intended mounting, and more important, the force required to effect flossing and to urge the floss through very tight teeth is such that even the methods which employ loops are not sufficiently reliable to hold the floss in place upon the flossing tool when the force required to work on subject teeth is applied. Ten pounds or more pressure upon a flossing tool can be necessary to insert or remove a strand of floss from between very tight teeth and in use the flosser is pushed and pulled in several directions causing great forces to be effected upon the floss from many angles.

Working example of existing designs show that the holding in place of the strand of floss upon the flossing tool is a major problem which must be overcome in order to increase efficiency and aid in the convenient use of flossers.

When in use such great force in urging the floss between the teeth has the tendency to distort the shape of the flossing tool, especially if the tool is made of plastic or other flexible material, which then allows the floss to pull loose or to derail from its mounting, thus effectively limiting the utility of prior flossers in the purposes for which they were designed.

SUMMARY OF THE INVENTION

The purpose of this invention is to provide an inexpensive disposable flossing tool which affords the user the benefits of leverage action through fulcrum means, causing the floss to remain taut as needed while in use, wherein said tool is manufactured in such a way as to hold the floss firmly in its intended place, and withstand the pressures placed upon the framework when the flosser is in use and have no possibility of floss derailing from its mounting or separating from its holder.

It is an object to accomplish this by integrating a loop of floss within the framework of a fulcrumed flosser. It is a further object to show how the tool can be made cheaply enough to be disposable, thus when the floss is used up, or breaks through use, the user simply gets a fresh tool, with fresh floss.

It is a major advantage of the design that the floss cannot remove itself from the tool even when the tool is greatly stressed or distorted, allowing the user to clean interdental spaces between very tight teeth with ease and confidence.

The design is substantially similar to that of the "Disposable Flossing Tool Featuring Leverage Action" described in my filing U.S. application Ser. No. 07/421,352, of which this application is a continuation in part, except the original strand of floss affixed at the ends of the two substantially parallel frame members is replaced by a continuous loop of floss which is embedded into the framework, and therefore the loop of floss is integrated with the portion of the frame which holds the floss.

Said loop of floss may be manufactured as needed either as whole loops of the required size, or tied to form a loop of a desired size prior to tool assembly.

By integrating the loop of floss into the frame via molding the plastic framework around the floss, the floss will not separate from the frame when in use and under The configuration of the frame design is in the general shape of the capital letter "H", permitting the user to grasp one end of the tool, which is the end opposing the end at which the working portion of the floss is exposed, and a central perpendicular cross member acts as effective fulcrum means.

The framework has the ability then to be held in the hand or between the fingers of the user and when the ends of the substantially parallel members are squeezed toward each other at the end which is held, the opposing ends at which the working portion of the loop of floss is exposed are drawn apart, causing the exposed floss to be stressed, and it therefore becomes taut, such that it may be used in the fashion described herein to floss one's teeth.

Said stressing action will be best achieved by a plastic construction which is rigid and sturdy, yet having a degree of flexibility such that indicated leverage action may be effective for the purposes described. Installation of the loop of floss may be done by placing the loop into the tool mold before injecting plastic into the mold, or molding the frame in half sections, and inserting the loop of floss as described between the halves, and then joining the halves, completing the manufacture.

Since the loop of floss is continuous, it is not necessarily a requirement of manufacture that the floss be glued, affixed or molded solidly within the frame, because if the loop runs in a channel through the frame, then no separation of the frame and loop can occur without structural fracture of the floss loop or the frame components.

Therefore great structural strength of the tool is created. The instrument may break if overly stressed, or the floss may break through use, but in normal use separation of the floss from the tool frame is much less likely.

DESCRIPTION OF THE INVENTION

Figure 1:
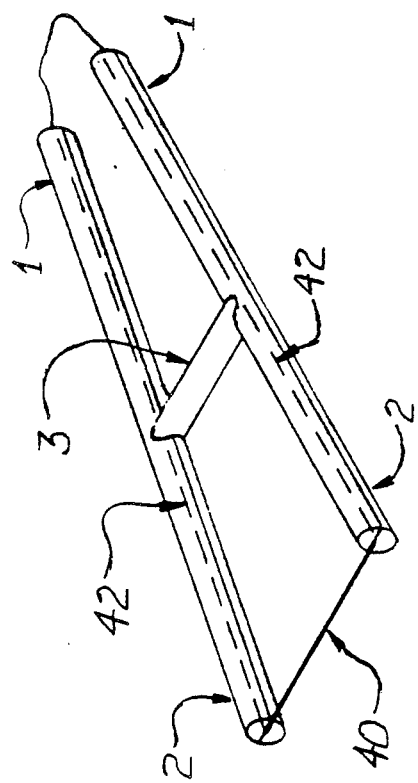

FIG. 1. flossing tool including crossmember, showing leverage action.

FIG. 2. preferred embodiment of tool wherein fingertip manipulation provides a fulcrum for leverage action.

FIG. 1. Turn now your attention to FIG. 1. Parallel to each other are two frame members, labeled 1 at the end which is to be held in the user's grasp, and 2 at the end which contains, the exposed working portion of the floss loop, 40. The floss loop, collectively 40 and 42, is continuous, and therefore is integral and passes through the parallel frame members.

The hand held flossing tool is grasped between fingers at the ends 1, and squeezed to begin leverage action. As the ends 1 are brought together, the ends 2 are drawn apart by leverage action acting on the substantially fixed fulcrum, 3, thus the exposed working portion of the floss loop, 40, is stressed and pulled taut. Regardless of the pressure brought to bear upon the floss, up to the point of breakage of the components of the frame and floss loop, separation of the floss from the framework is not possible, therefore providing superior strength of design in a periodontal hygiene tool.

FIG. 2. A preferred embodiment is double-ended, and is hand held such that a user's fingers control and effect the leverage action to stress the floss and cause tautness. This double-ended tool can be fulcrumed by a cross member at space 32 if desired. When grasped at either end, a short working length of dental floss, 40, is easily leveraged at the opposite end. If the crossmember is omitted, a fingertip placed in the space 32 acts as a fulcrum, and manipulation of the two rigid members, 12, provides leverage action to the floss, 40, at the end opposite the user's grasp.

The loop of floss, 42, embedded in the two rigid members, 12, and the two short exposed working portions, 40, on each end of the tool illustrated in FIG. 4 is the most effective floss loop design because it doubles the amount of use before the tool should be disposed and is easy to manufacture: Place a floss loop (approximately 7 or 8 inches total length) so that it runs lengthwise through two small (approximately 3 inches × 0.08 inch diameter) rod molds that are substantially parallel, and fill the molds with an injection molding material to create the tool as shown in FIG. 4.

What is claimed is:

1. A double-ended hand held dental flossing tool, comprising a loop of floss and two substantially parallel members, whereby said loop is integral with said members and provides two short working lengths of floss exposed at opposing ends of said members whereby a fingertip placed between the members provides a fulcrum such that said working lengths of floss may be stressed by leverage means whereby fingertip manipulation effects said leverage means.

2. A tool of claim 1 further comprising a crossmember, substantially perpendicular to said two substantially parallel members, whereby said cross member provides said fulcrum whereby said leverage means are effected.

* * * * *